(12) United States Patent
Trespalacios (10) Patent No.: US 8,011,018 B2
(45) Date of Patent: Sep. 6, 2011

(54) GARMENT PROTECTOR

(76) Inventor: Gabriella Trespalacios, Coto de Caza, CA (US)

(*) Notice: Subject to any disclaimer, the term of this patent is extended or adjusted under 35 U.S.C. 154(b) by 287 days.

(21) Appl. No.: 12/426,146

(22) Filed: Apr. 17, 2009

(65) Prior Publication Data

US 2010/0263102 A1    Oct. 21, 2010

(51) Int. Cl.
*A41D 27/13* (2006.01)
(52) U.S. Cl. .................................. 2/53; 2/46
(58) Field of Classification Search .............. 2/53, 46, 2/54–58, 231, 406, 62, 104, 463, 459, 20, 2/60, 47, 51, 465, 24, 267, 268; 604/385.201, 604/380, 379, 385.01, 385.03, 385.07, 385.101; D2/860; 450/37, 39, 55, 56, 57
See application file for complete search history.

(56) References Cited

U.S. PATENT DOCUMENTS

| | | | | |
|---|---|---|---|---|
| 812,486 | A | * | 2/1906 | Dix .............................. 604/392 |
| 947,698 | A | * | 1/1910 | Hinckley ......................... 2/53 |
| 1,691,348 | A | | 11/1928 | Hanauer |
| 1,730,762 | A | * | 10/1929 | Furst ................................ 2/53 |
| 2,023,183 | A | * | 12/1935 | Rath ................................. 2/53 |
| 2,269,365 | A | * | 1/1942 | Fowler ............................. 2/53 |
| 2,535,864 | A | * | 12/1950 | Plehn ............................. 450/55 |
| 2,556,231 | A | * | 6/1951 | Stephens ......................... 2/53 |
| 2,573,346 | A | * | 10/1951 | Madsen ........................... 2/55 |
| 3,141,174 | A | * | 7/1964 | Meier-Nieper .................. 2/53 |
| 3,156,924 | A | * | 11/1964 | Wonacott ........................ 2/53 |
| 3,345,643 | A | * | 10/1967 | Bradley ........................... 2/53 |
| 3,885,247 | A | | 5/1975 | Kost |
| 4,059,114 | A | * | 11/1977 | Richards ....................... 604/359 |
| 4,393,521 | A | | 7/1983 | Jones |
| 4,485,492 | A | * | 12/1984 | Sneider ............................ 2/56 |
| 4,631,752 | A | | 12/1986 | Heyman et al. |
| 4,747,162 | A | | 5/1988 | Yanagihara |
| 4,773,905 | A | * | 9/1988 | Molee et al. ................ 604/378 |
| 5,042,088 | A | | 8/1991 | Sherrod et al. |
| 5,103,500 | A | | 4/1992 | Nager et al. |
| 5,790,982 | A | | 8/1998 | Boutboul et al. |
| 5,864,889 | A | | 2/1999 | Suffern |
| 5,884,330 | A | | 3/1999 | Erlich |
| 6,269,486 | B1 | | 8/2001 | Nager et al. |
| 6,760,920 | B1 | | 7/2004 | Kadymir et al. |
| 2007/0150995 | A1 | | 7/2007 | Luna |
| 2010/0180357 | A1 | * | 7/2010 | Hofer et al. ...................... 2/53 |

FOREIGN PATENT DOCUMENTS

DE    202007008283    *    9/2007

OTHER PUBLICATIONS http://www.fashionsanity.com, "Garment Guard Disposable Underarm Sweat Pads Shields", Garment Guard Disposable Underarm Shields, 2 pages, Jan. 10, 2008, accessed on Jul. 14, 2009. http://www.advantagewear.com/info-dress-shields.html, 5 pages, DRI-SHIELDS®, accessed on Jul. 14, 2009.
http://www.laurensilva.com/Braza_Disposable_Dress_Shields_p/braz-s-fslash-301x.htm, "Braza Disposable Dress Shields Style S/301x", 2 pages, accessed on Jul. 14, 2009.
http://www.sweatex.com/howto.htm, "How to use Sweatex", 2 pages, accessed on Jul. 14, 2009.
Kleinert's 2009 Catalogue, 8 pages, 2009.

* cited by examiner

*Primary Examiner* — Amy B Vanatta
(74) *Attorney, Agent, or Firm* — Knobbe, Martens, Olson & Bear, LLP (57) ABSTRACT

A garment protector is configured to absorb moisture and to thereby preserve a garment of a user. The garment protector can have a pad attached to the garment. The pad can absorb moisture and reduce or prevent moisture from staining the garment. The garment protector can have multiple layers to perform these functions. The garment protector can have one or more application channels. The application channel can span a seam and the associated cross-stitching of a garment so as not to add bulk at the seam that a pad would if over the seam.

20 Claims, 7 Drawing Sheets

GARMENT PROTECTOR

BACKGROUND OF THE INVENTION

1. Field of the Invention

The invention relates generally to improvements in garment protectors and methods to protect clothing from perspiration. In particular, the invention is related to garment protectors for the underarm area of a shirt or blouse.

2. Description of the Related Art

It has long been known that perspiration can discolor and damage clothing. In addition, it can be undesirable to allow perspiration to penetrate or show through clothing. Sweat can be the cause of embarrassment as well as discomfort in social situations. Sweat marks can leave clothing stained, smelly and drab. For these reasons, various antiperspirants and pads have been developed to reduce or hide perspiration, especially in the underarm area of the body.

Such products can beneficially prevent or reduce the problems associated with perspiration. Underarm pads can also provide further protection to work with antiperspirants to help reduce the risk of perspiration showing through clothing. The use of underarm pads in conjunction with antiperspirants or deodorants can increase the comfort level of the wearer and reduce the need to change top garments after prolonged use. Also, underarm pads can prolong the useful life of clothing by absorbing underarm moisture and reduce cleaning expenses, such as, dry cleaning bills.

While current designs of underarm pads offer several benefits, they can be difficult to apply, bulky in shape and therefore restricting and undesirable to wear. Additionally, current designs may not move properly with the clothing to which they are attached resulting in detachment causing embarrassment. Furthermore, current underarm pads have been designed as 'specialty items' which tend to be expensive and therefore unattainable by the common wearer. As such, there exists a need for an improved garment protector.

SUMMARY OF THE INVENTION

A garment protector can be attached to the underarm area of a shirt or blouse and thereby protect the clothing from perspiration. The garment protector can be a pad including a woven padding layer, a layer of absorbent cotton and an adhesive backing. The garment protector can have two application channels made of a flexible material that can allow the garment protector to take the shape of and move with the shirt or blouse allowing for regular motion or exercise. The garment protector can adhere to both the arm and body of the garment. The application channels can overlay the cross-stitching of the garment without adding substantial bulk. The application channels can be thin flexible members. The application channels can also have enhanced adhesion to ensure proper and secure application and wearability. The application channels can have visible application lines to facilitate the proper placement of the garment protector.

In some embodiments, a garment protector for preserving a piece of clothing can comprise a first channel, a second channel and first, second, third and fourth layered sections. Each layered section can comprise a comfort layer, an absorbent layer, and an adhesive layer. The first channel can separate the first and second layered sections from the third and fourth layered sections and the second channel can separate the first and fourth layered sections from the second and third layered sections. The channels can be flexible and can have a thickness less than the thickness of the layered sections. In certain embodiments of the garment protector, the width of at least one channel allows the channel to span cross-stitching of a seam in the piece of clothing so as not to add to the bulk at the seam that a layered section would if placed or located over the seam.

Additional embodiments can provide a garment protector for preserving a piece of clothing comprising a first channel, a second channel and first, second, third and fourth absorbent sections. The first channel can separate the first and second absorbent sections from the third and fourth absorbent sections and the second channel can separate the first and fourth absorbent sections from the second and third absorbent sections. The channels can be flexible and can have a thickness less than the thickness of the absorbent sections and a width that allows at least one of the channels to span a cross-stitching of a seam in the piece of clothing so as not to add to the bulk at the seam that one of the absorbent sections would if over the seam. The channels can also be configured to allow the absorbent sections to move in different directions and orientations from one another.

In some embodiments, the first channel can be configured for use at a seam between an arm and a body of the piece of clothing. In some embodiments, the second channel can be configured for use at a seam along the arm and along the body of the piece of clothing and the first channel can allow for greater flexibility than the second channel.

In certain embodiments, a garment protector for preserving a garment can comprise a first channel, a second channel and a pad for absorbing moisture in an underarm area of the garment. The first channel can be configured to attach to the garment along a first seam between an arm and a body of the garment. The first channel can span the first seam such that the pad is on either side of the first seam but not on the first seam. The second channel can be configured to attach to the garment at a second seam, the second seam being along the arm of the garment and at a third seam, the third seam being along the body of the garment. The second channel can span the second and third seams such that the pad is on either side of the second and third seams but not on the second or third seams. The first channel can be wider than the second channel and the first and second channels can be thinner than the pad.

DETAILED DESCRIPTION OF THE PREFERRED EMBODIMENTS

Figure 1:
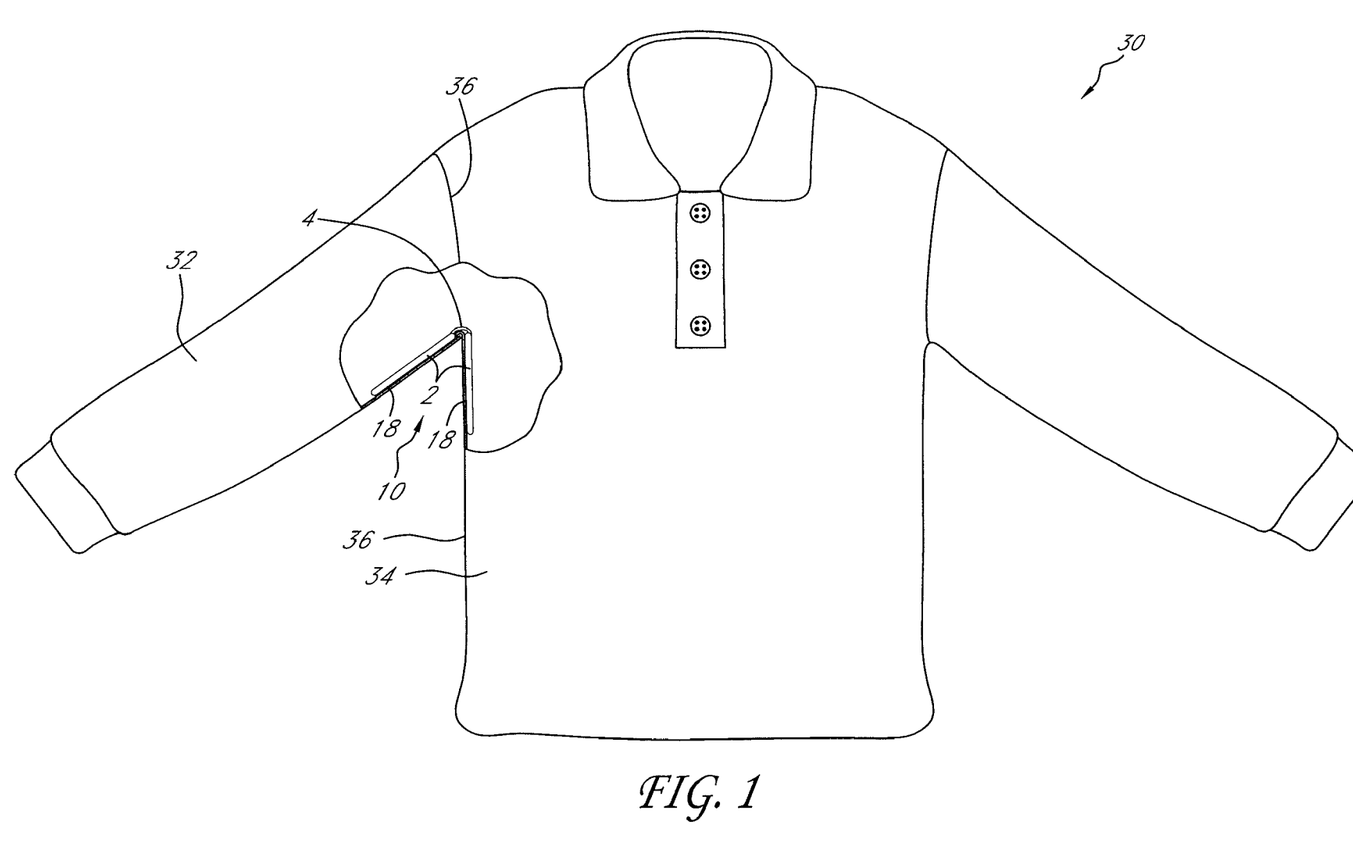
FIG. 1 shows a shirt with a cut-away view in the underarm area of the shirt, the cut-away view showing a cross-section of an embodiment of a garment protector attached to the shirt along a seam where the sleeve and body of the shirt are attached.

As shown in FIG. 1, a garment protector 10 can be attached to a garment or piece of clothing 30 to thereby protect the garment from perspiration. Preferably, the garment protector 10 attaches directly to the inside of the article of clothing 30. For example, FIG. 1 illustrates a garment protector 10 attached to an underarm region of a shirt or blouse. The garment protector 10 could also be used in a dress, robe, jacket, sweater, coat, etc. As additional examples, a garment protector 10 can be attached to a groin region of a pair of pants, shorts, panties or underwear.

FIG. 1 further shows a garment protector 10 that comprises a pad 2 and an application channel 4. In some embodiments, the pad 2 is configured to absorb moisture, such as perspiration. The pad 2 can be made of a flexible material that can allow the garment protector 10 to take the shape of and move with the garment 30 to which the garment protector 10 is attached.

Figure 2:
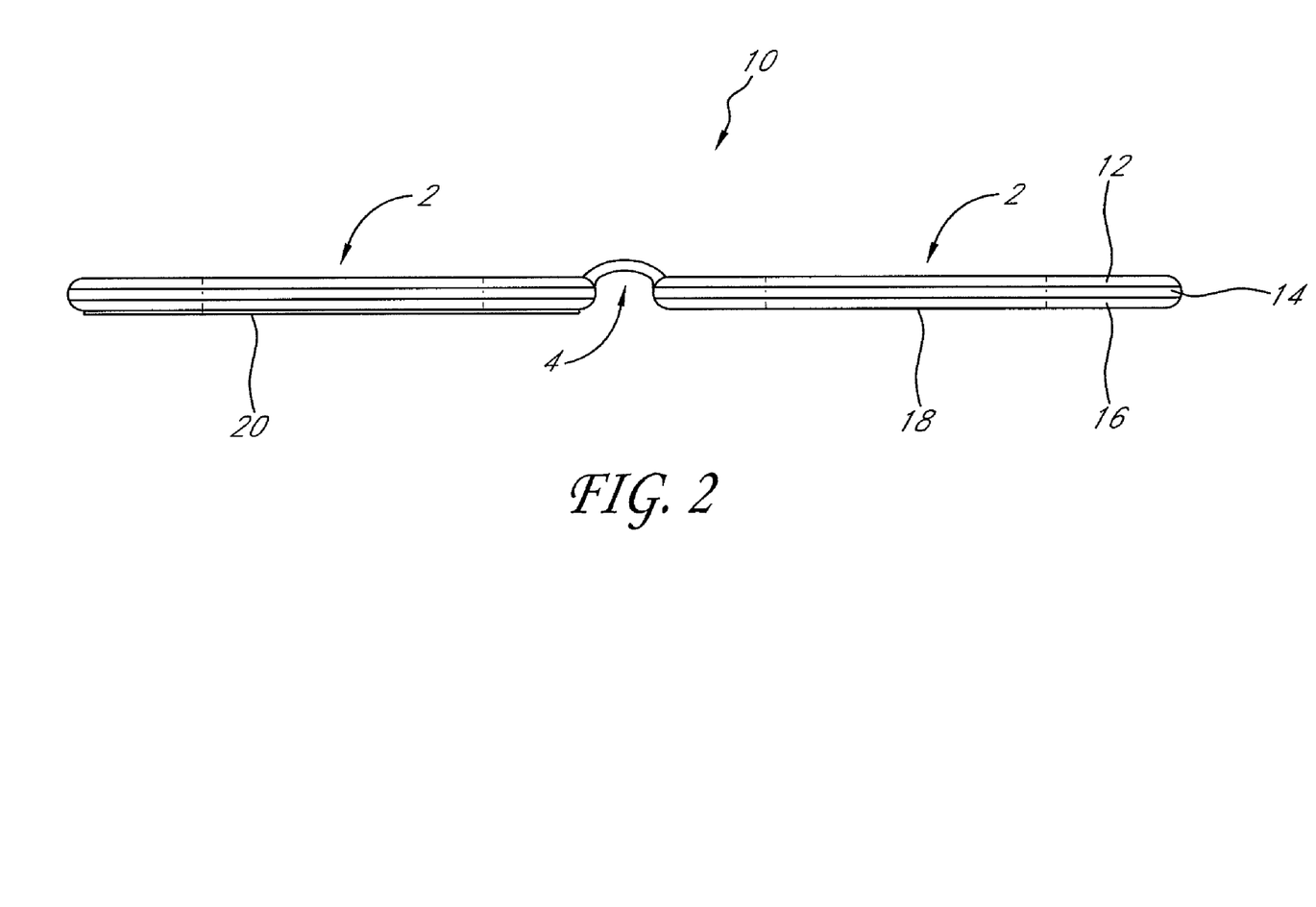
FIG. 2 illustrates a cross-sectional view of a side of a garment protector with multi-layered pads.

Moving now to FIG. 2, a cross-section of an exemplary embodiment of a garment protector 10 with two multi-layered pads 2 and an application channel 4 is shown. In some embodiments, the multi-layered pad 2 has a comfort layer 12, an absorbent layer 14, a boundary layer 16 and an adhesive layer 18.

The different layers of the multi-layered pad 2 will now be discussed. Preferably, the comfort layer 12 comprises a layer of padding to increase the comfort of the garment protector 10. The comfort layer 12 can also be configured to increase the comfortable feel of the garment protector 10 against the skin of a user. For example, a woven padding can be used to create this effect. FIG. 2 shows the comfort layer 12 as the top layer of the garment protector 10, configured for direct contact with the body of a user. In some embodiments, the comfort layer 12 allows perspiration to travel through the layer. Alternatively, the comfort layer 12 may wick perspiration away from the user.

Certain embodiments of the comfort layer 12 are made from a variety of different materials or blends of materials. Additionally, examples of the comfort layer 12 include a solid material, a tightly woven material, a loosely woven material and/or a material with holes or gaps so that parts of certain other layers, such as the absorbent layer 14, can be exposed. According to certain embodiments, the comfort layer 12 can be treated with a chemical or other substance. In some embodiments, the comfort layer 12 can be pretreated prior to assembling the garment protector 10 or the multi-layered pad 2. Examples of treatments can include a comfort layer 12 treated with an antiperspirant, deodorant or fragrance compound. The comfort layer 12 can also function as a medication delivery mechanism. The comfort layer 12 can be skin color or other desirable color or colors. This can, for example, help to prevent the pad from showing through the garment.

Still referring to FIG. 2, an absorbent layer 14 of an absorbent material to absorb moisture or perspiration is shown. As illustrated, the absorbent layer 14 is directly under the comfort layer 12 and between the comfort layer 12 and the boundary layer 16. In other embodiments, the absorbent layer 14 can be in a different configuration, such as in direct contact with the adhesive layer 18. Alternatively, in certain embodiments the comfort layer 12 and absorbent layer 14 are combined into a single homogeneous layer.

The absorbent layer 14 can comprise, for example, a layer of cotton or an absorbent cotton pad. As such, the absorbent layer 14 can be 100% cotton or a blend of cotton and other materials. Preferably the absorbent layer 14 is quick drying. According to certain embodiments, the absorbent layer 14 is treated with a chemical or other substance. In some embodiments, the absorbent layer 14 can be pretreated prior to assembling the garment protector 10 or the multi-layered pad 2. For example, the absorbent layer 14 can be treated with a deodorant, antiperspirant or a fragrance compound. Other possible examples of treatments include: treatments to increase a quick drying effect and treatments to reduce odor. The absorbent layer 14 can also function as a medication delivery mechanism. The absorbent layer 14 can be skin color or other desirable color or colors. This can, for example, help to prevent the pad from showing through the garment.

The adhesive layer 18 can comprise a layer of adhesive which in some embodiments is in the form of a sheet of adhesive such as a piece of tape or a layer of glue. The adhesive layer 18 allows the garment protector 10 to removably attach to an article of clothing 30, as shown in FIG. 1. In various embodiments, the adhesive layer 18 covers the entire back side of the garment protector or the entire side of the pad opposite the comfort layer 12 or other parts of the back side. For example, the adhesive layer 18 in the form of strips of adhesive could be placed in predetermined locations to cover parts of the back side.

In some embodiments, the adhesive layer 18 can comprise different types of adhesives at different locations on the back side of the garment protector 10. For example, the adhesive layer 18 can have a first adhesive covering most of the back side and a second adhesive around the edges of the garment protector 10. The second adhesive can be an enhanced adhesive, i.e. an adhesive that is stronger or more adhesive than the first adhesive. In other embodiments, the first adhesive can be stronger than the second adhesive.

Some embodiments of the adhesive layer 18 are skin color, transparent or other desirable color or colors. The adhesive layer 18 can be configured such that it does not leave a residue on the piece of clothing 30 and that it adheres securely to all types of fabrics, textiles and other surfaces.

With continued reference to FIG. 2, certain embodiments of the multi-layered pad 2 further comprise a boundary layer 16. As shown in FIG. 2, the boundary layer 16 divides the multi-layered pad 2 such that a boundary is provided with the comfort layer 12 and absorbent layer 14 on one side and the adhesive layer 18 on the other. As explained above and as seen in FIG. 1, the adhesive layer 18 attaches to the article of clothing 30, thus the boundary layer can prevent or hinder moisture absorbed by the garment protector 10 from passing to the article of clothing 30. One way to perform this function is with a waterproof boundary layer 16. A thin flexible piece of plastic and a thin plastic film are examples of materials that can be used to form the boundary layer 16, although other materials may also be used.

The boundary layer 16 can have an adhesive backing making up the adhesive layer 18. In some embodiments, the boundary layer 16 and the adhesive layer 18 are combined. For example, the adhesive itself can form a boundary between the pad 2 and the article of clothing 30. Similar to the other layers, the color of the boundary layer 16 can be skin color or other desirable color or colors or transparent.

The boundary layer 16 can be a breathable material or manufactured in such a way so as to be breathable. Advantageously, a breathable boundary layer 16, as part of a breathable pad 2, may help minimize the effects of adding material to an area with a high propensity for perspiration, such as the underarm area of the body. This can also contribute to a quick drying ability of the garment protector 10.

In certain embodiments, the garment protector 10 further comprises a removable backing 20 to cover the adhesive layer 18. FIG. 2 illustrates a garment protector 10 that is being prepared for use. Where the removable backing 20 has been removed from one pad 2 but is still present on the other pad 2.

The removable backing 20 is preferably made from a thin sheet of plastic or paper but, can be made from many different materials. The backing 20 may be disposable.

Figure 3:
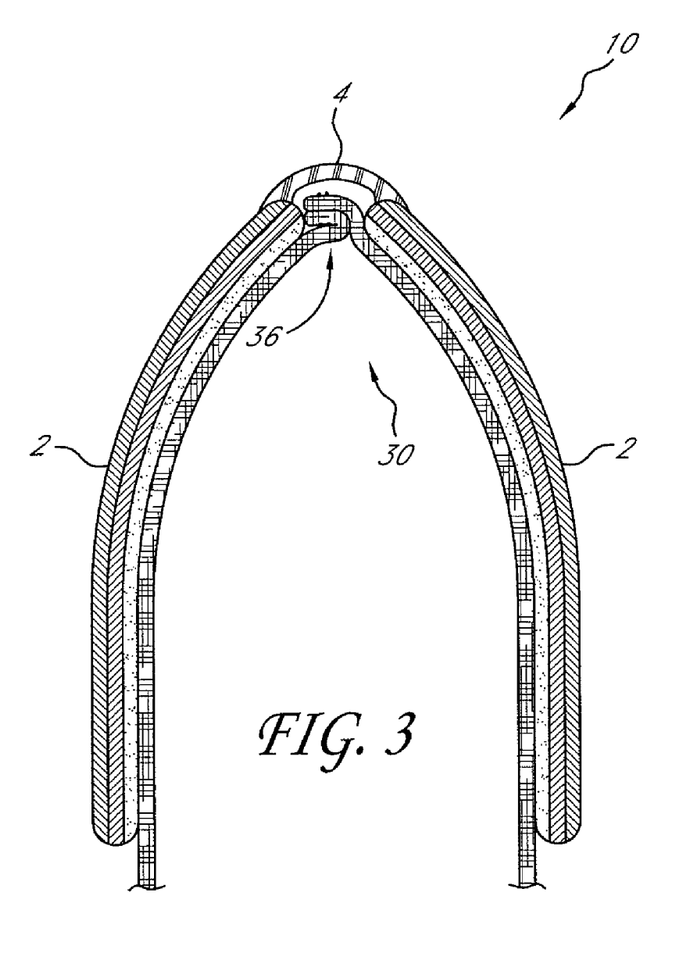
FIG. 3 shows a detail cross-sectional view of an embodiment of a garment protector attached to a shirt and also shows the alignment of a channel over a seam of the shirt, similar to the configuration of FIG. 1.

Referring now to FIGS. 2 and 3, the application channel 4 will be discussed. An application channel 4 can divide the garment protector 10 into two or more pads 2. In some embodiments, the garment protector 10 can comprise two or more application channels 4 which can divide the garment protector 10 into additional pads 2. Some other embodiments comprise two application channels 4 and three pads 2. Still other embodiments comprise any number of different configurations of application channels 4 and pads 2.

The application channels 4 can be made of a flexible material that allows the garment protector 10 to take on the shape of and move with the garment 30 to which the garment protector 10 is attached. Thus, the application channels 4 can conform to the contours of the garment 30.

For example, FIG. 3 shows a portion of a garment 30 with a seam adjacent the channel 4 when a garment protector 10 is attached to the garment 30. As can be seen, the pads 2 are attached to different parts of the garment 30 and the application channel 4 overlies the seam 36. One advantage of this embodiment is that the application channel 4 is thinner then the pads 2. This helps reduce the amount of material added on top of the seam 36. Also, by having the application channel 4 separate the pads 2, the pads 2 are able to more closely conform to the shape of the portion of the garment 30 to which they are attached, thereby eliminating bulk and providing more comfort for a wearer. Additionally, the application channel 4 can facilitate the ability of the garment protector 10 to adhere to the different parts of the garment 30 and to both move and bend with the garment 30. This is because the pads 2 are separate and so they can more easily move separately. This can also be a result of the flexibility of the application channels 4. The application channels 4, of some embodiments, cradle the seam of a garment with great flexibility to move with the seam. This allows the pads 2 to remain in place on the garment and increase the usability of the garment protector 10.

A seam 36 in a garment typically has extra fabric in addition to the extra material added by cross stitching and sewing the seam 36 together. It can be undesirable to add too much additional material on top of the seam 36. At the same time, it can be desirable to have a garment protector 10 at the seam 36 because typically seams 36 are found in clothing in the same areas that have a propensity for perspiration, such as the underarm area and the groin region. Thus, by having an application channel 4 that is thinner than the pads 2 a user can obtain a proper balance between having a reduced amount of material on top of the seam 36 and ensuring the proper placement of the garment protector 10 where it is needed most.

As mentioned previously, the application channel 4 can be thinner than the pad 2. For example, in some embodiments where the pad 2 is a multi-layered pad, the application channel 4 has less layers then the pad 2, such as one layer. In some embodiments, the application channel 4 can be a thin flexible member. Alternatively, the application channel 4 can have multiple layers that are thinner than the pad 2. In some embodiments, the application channel 4 can comprise one or more of the layers of a multi-layered pad 2. For example, the application channel 4 could be made from the same material as the boundary layer 16 or the comfort layer 12. In certain embodiments, the application channel 4 is made from the comfort layer 12 and the boundary layer 16.

An application channel 4 made of one or more of the layers of a multi-layered pad 2 can be formed by applying pressure and/or heat to the particular section of the pad 2. This can decrease the height of the material in this area and can change certain characteristics of the material or materials. For instance, the heat and/or pressure can combine what were once two or more layers into essentially one layer or a combination of layers that acts as one layer. One characteristic that can change is an increase in the flexibility of this section of the pad that then becomes the application channel 4.

By minimizing the application channel 4 as a thin flexible member (see the cross-sectional view of FIG. 3) there can be no doubling up in the seam area 36 compared to the rest of the underarm area. Thus, there is no added thickness or other problems that may result from multiple layers on top of a seam 36. This can also help reduce a perceived feeling of bulkiness and discomfort of the garment protector 10 experienced by the user compared to what the user would experience with a pad 2 or a multi-layered pad 2 covering the seam 36.

The application channel 4 can cover a length of a seam 36. Whether one or more application channels 4 are used, the application channels 4 can be configured for use with a seam 36 in a particular region of a garment 30.

As discussed previously, the adhesive layer 18 of some embodiments can cover the entire back of the garment protector 10. This can include the application channel(s) 4. Application channels 4 of certain embodiments have adhesive on their back sides. This adhesive can be the same adhesive as the adhesive layer 18, or a different adhesive. In a preferred embodiment, the adhesive on the application channel is an enhanced adhesive that is stronger than the adhesive on the pad. The enhanced adhesive on the application channel 4 combined with the greater flexibility of the application channel 4 verses the pad 2, helps to ensure the garment protector 10 stays in place and moves properly and naturally with the user's movements.

Figure 4:
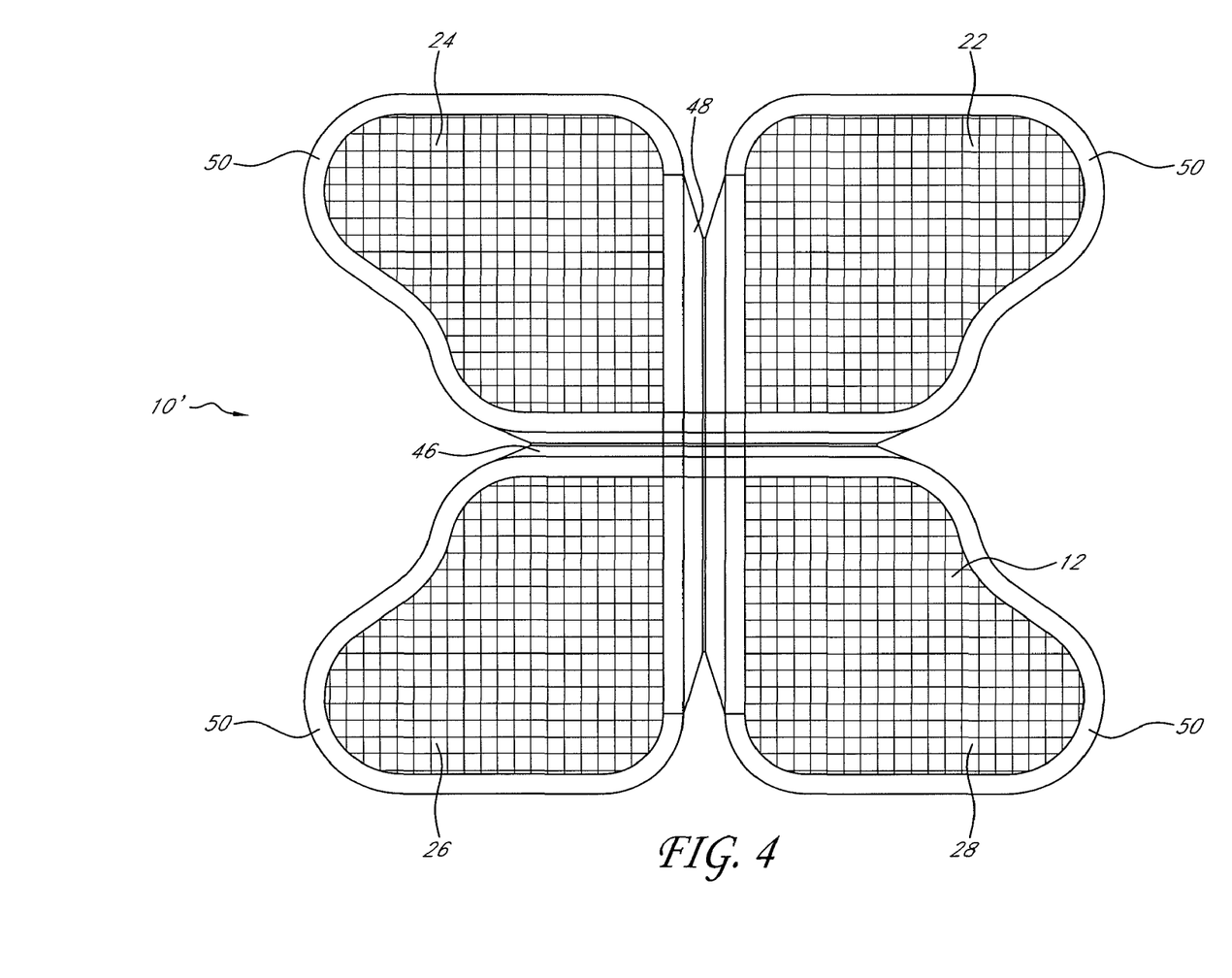
FIG. 4 shows a front view of an exemplary garment protector according to a preferred embodiment.
Figure 5:
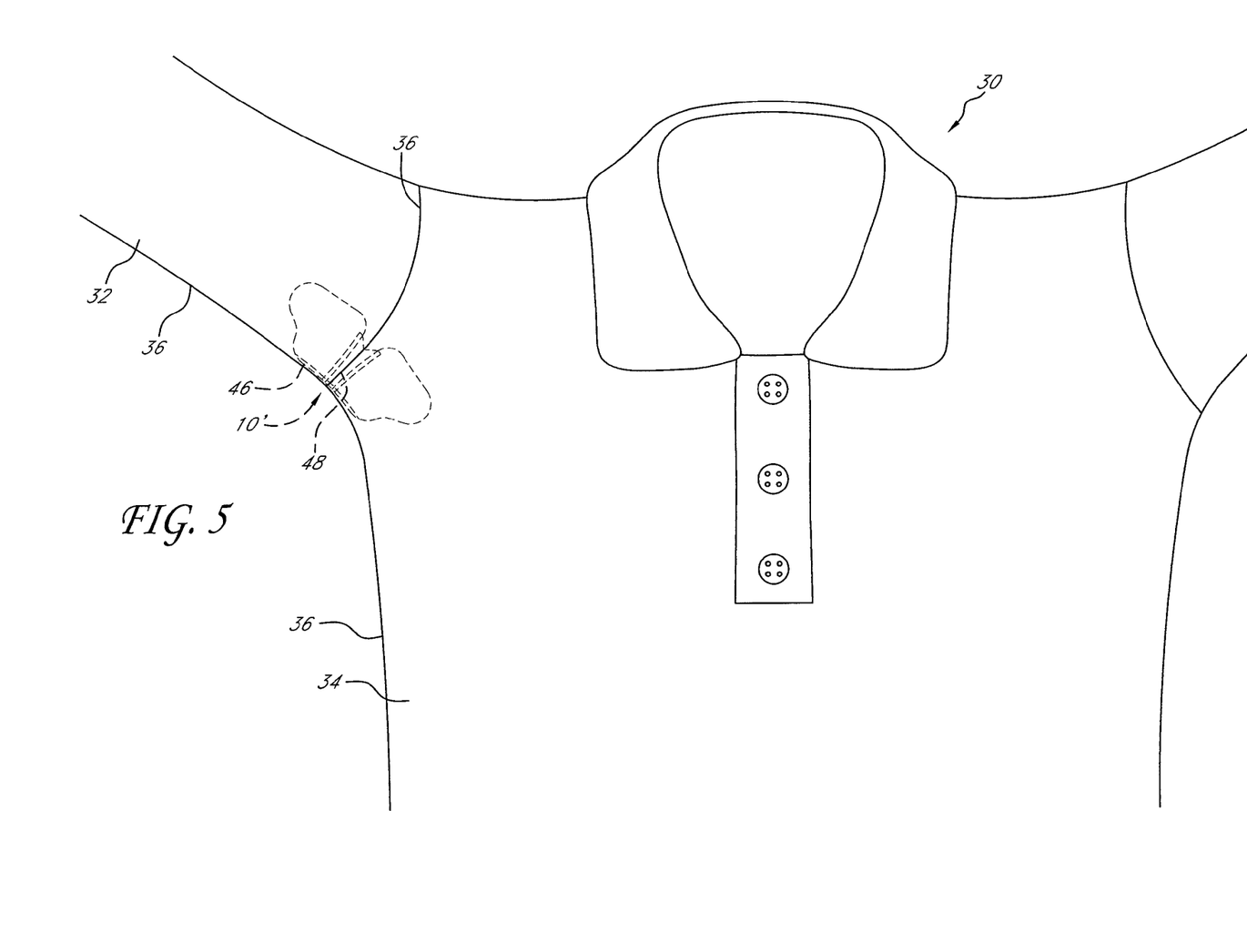
FIG. 5 is a view of a garment with the garment protector of FIG. 4 attached to the garment and showing an embodiment of the orientation and positioning of the garment protector in the garment at the underarm area of the garment.
Figure 6:
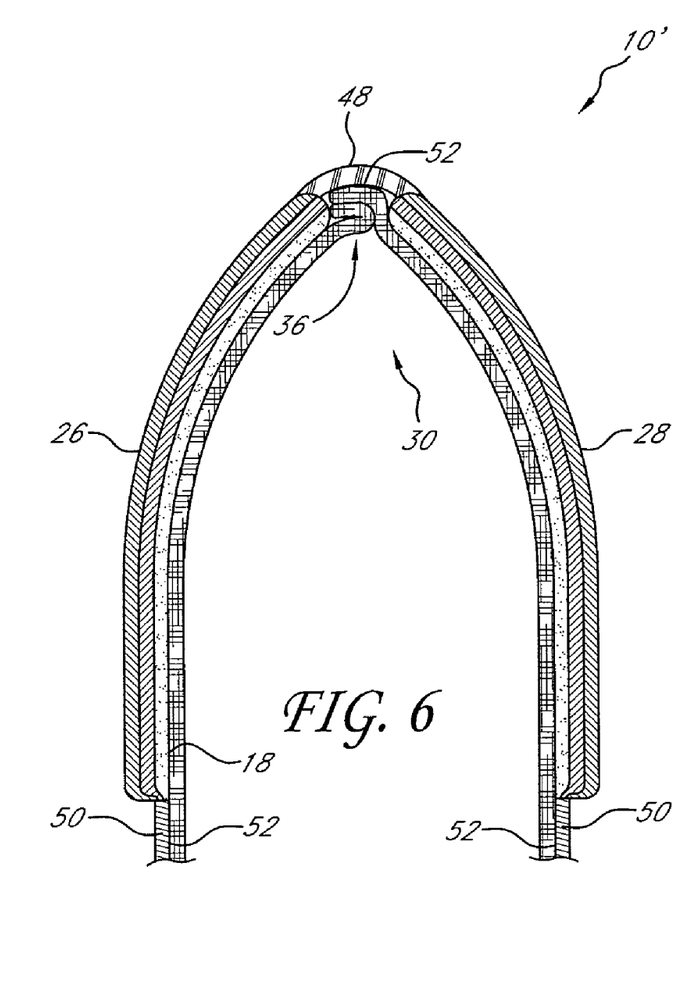
FIG. 6 shows a detail cross-sectional view of the garment protector of FIG. 4 attached to a shirt.

FIG. 4 shows an embodiment of a garment protector 10' with two application channels 46, 48 which divide the garment protector 10' into four pads 22, 24, 26, 28. The embodiment of FIG. 4 can be configured for use in the underarm area of a garment 30, as shown in FIGS. 5 and 6. FIG. 5 illustrates the first application channel 46 configured for use at the seam 36 where the arm 32 of the garment 30 connects with itself and where the body 34 of the garment 30 connects with itself. The second application channel 48 is preferably configured for use at the seam 36 where the arm 32 of the garment 30 attaches to the body 34 of the garment 30. The application channels 46, 48 are shown covering a length of part of the seams 36 on the garment 30. In some embodiments, the four pads 22, 24, 26, 28 of the garment protector 10' can be multi-layered pads as discussed previously.

In some embodiments, the garment protector 10' can adhere to both the arm 32 and body 34 of the garment 30. The application channels 46, 48 can facilitate the ability of the garment protector 10' to both adhere to different parts of the garment 30 and to both move and bend with the garment 30. This can be very important as the underarm area of a shirt or blouse 30 is typically where the arm 32 and the body 34 of the garment 30 meet and an area that experiences a substantial amount of movement. This area can be constantly changing position as the user goes about his/her daily tasks. As the garment protector 10' is forced into different orientations, the application channels 46, 48 can allow the garment protector 10' to remain flexible and remain in place even under extreme conditions.

Still referring to FIGS. 4, 5 and 6, as the underarm area of a garment is generally a location with multiple seams 36, the associated cross-stitching and extra fabric, the application channels 46, 48 can be designed to overlay the seams 36 without adding substantial bulk. This can be seen especially in FIG. 6. FIG. 6 also illustrates application channel 48 with an adhesive 52. The adhesive 52 can be seen contacting the seam 36. In some embodiments, the adhesive layer 18, discussed previously, can be comprised of a regular adhesive applied over the back side of the four pads 22, 24, 26, 28 and an enhanced adhesive 52 is applied over the application channels 46, 48 and layered over the seam providing a secured application. Adhesive on the application channel can provide the benefits discussed above, such as, working with the greater flexibility of the application channel to ensure the garment protector 10' stays in place.

In some embodiments, the first and second application channels 46, 48 can be similar in size. In some embodiments, such as that shown in FIG. 4, the second application channel 48 is wider than the first application channel 46. For example, in some embodiments, the second application channel 48 is twice as wide as the first application channel 46. In some embodiments, the first and second application channels 46, 48 can be made from different materials. For example, one material can be more flexible than the other.

It can be desirable to make the second application channel 48 wider and/or more flexible than the first application channel 46 to increase the flexibility of one of the application channels over the other. This can be warranted, for example, where one seam is likely to experience greater movement than another. In the example of the underarm area of a shirt 30, the application channel 48 over the seam 36 connecting the sleeve 32 and the body 34 of the shirt may experience more movement than the application channel 46 over the seams 36 in the sleeve 32 and body 34 of the garment 30. In addition, a garment protector 10, 10' is likely to be folded over itself along the sleeve 32 and body 34 connecting seam 36 at certain times and then unfolded at other times. For example, FIG. 5 shows a garment protector 10' in the position when it is not folded over itself while FIG. 1 shows a garment protector 10 that is folded over itself.

Looking at FIGS. 4 and 6, a garment protector 10' can have an edge 50. The edge 50 can be formed in various ways. In some embodiments, the edge 50 can be made in the same or in a similar manner as discussed above regarding the application channel. This can include, but is not limited to applying pressure and/or heat to the material.

Like the application channel, in certain embodiments, the edge 50 is formed from one or more layers of the pad. In some embodiments, the edge 50 is formed from the top and bottom layers of the pad. This could preferably be, for example, the boundary layer 16 and the comfort layer 12. Using the top and bottom layer advantageously seals and contains the layers within the pad. In some other embodiments, the edge is formed of all of the layers of the pad. The edge 50 can be thinner than the pad as shown in FIG. 6. This can be a result of the method of forming, or because of the materials used to form the edge 50. In addition, the edge 50 can be formed of multiple layers but act as one layer because of the forming process.

FIG. 6 shows the edge 50 backed by an adhesive 52 but it can also be backed by the adhesive layer 18. The adhesive backing on the edge 50 of some embodiments is an enhanced adhesive that is stronger than the adhesive backing the pad or comprising the adhesive layer 18.

Figure 7:
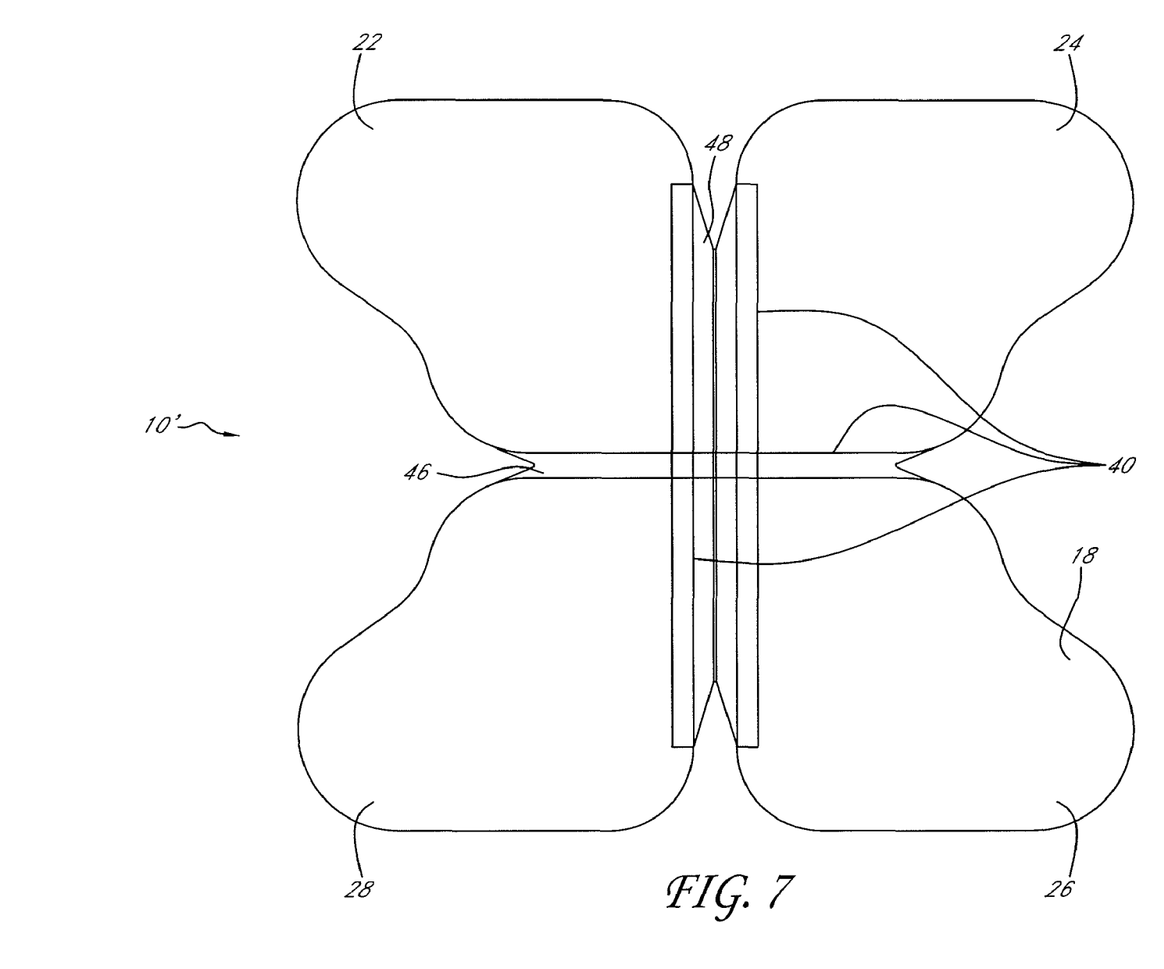
FIG. 7 illustrates a back view of the garment protector of FIG. 4.

Now turning to FIG. 7, the garment protector 10' can further comprise markings 40. The markings 40 can indicate the proper location or orientation to attach the garment protector 10 to a garment 30. In certain embodiments, the markings can be on the application channel 4, 46, 48. The markings 40 shown in FIG. 7 are a distinct pattern. In some embodiments, instructions included with the product indicate where to place the markings 40 in a garment 30. In other embodiments the markings 40 can include words and/or pictures.

The different embodiments of garment protectors 10, 10' can be a variety of different shapes. The garment protector 10, 10' can be shaped to appropriately fit a garment 30. For example, the garment protector 10' of FIG. 7 is shown as generally "X" shaped or butterfly shaped. FIG. 7 shows the garment protector 10' in the general shape of butterfly wings with pads 22 and 24 making up one of the wings and pads 26 and 28 making up the other wing. The design of FIG. 7 beneficially fits in the underarm area of a shirt or blouse 30 while reducing chaffing or interference with the user's body.

The pads of the garment protector 10, 10' also can be a variety of different shapes. Examples include: generally heart shaped or piano shaped. FIG. 7 shows the pads as generally piano shaped, i.e. region 24 is the shape of the top of a grand piano with the keyboard area along the second application channel 48.

The garment protector 10, 10' can beneficially be absorbent, thin, discreet, convenient, and disposable. The garment protector 10, 10' can be unisex and can provide protection from odors and moisture staining of clothing. The garment protector 10, 10' can reduce dry cleaning bills, prevent underarm stains and odors, prolong the life of garments and provide everyday freshness.

According to certain embodiments, the garment protector can be treated with a chemical or other substance. Part or the entire garment protector can also be pretreated prior to assembly. Examples of treatments can include antiperspirant, deodorant, fragrance compound, etc. The garment protector can also function as a medication delivery mechanism.

A garment protector 10, 10' can be attached to a garment in many ways. For example, in some embodiments a user can remove the backing 20 on the adhesive layer 18 of the garment protector 10, 10', such as paper strips, and apply the garment protector 10, 10' to the inside of the garment 30. In other embodiments, a user can remove the backing 20 on the adhesive layer 18 and line up the application channel(s) 4, 46, 48 with the seams 36, so as to cover the seams 36 with the application channel(s) 4, 46, 48 and press the adhesive layer 18 of the garment protector 10, 10' firmly into contact with the garment 30. In still other embodiments, a user can remove the backing 20, use the markings 40 to properly position and orient the garment protector 10, 10' so that the application channel(s) 4, 46, 48 are over the proper seams 36 and press the adhesive layer 18 of the garment protector 10, 10' firmly into contact with the garment 30. In some embodiments, the garment protector 10, 10' can be washable and/or reusable. In some embodiments, a garment protector 10, 10' may comprise a fastener to fasten the garment protector to the garment, such as, for example, snaps or VELCRO.

The garment protector can be manufactured in several sizes to fit small, medium or large garments and users. Additionally, the underarm pads can be packaged in a container or box as a multi-unit and/or multi-shape configuration to allow greater flexibility and cost effectiveness to the user.

While certain embodiments have been described, these embodiments have been presented by way of example only, and are not intended to limit the scope of the disclosure. Indeed, the novel methods and garment protectors described herein may be embodied in a variety of other forms; furthermore, various omissions, substitutions and changes in the form of the methods and garment protectors described herein may be made without departing from the spirit of the disclosure.

What is claimed is:

1. A garment protector for preserving a piece of clothing comprising:
   a first channel;
   a second channel; and
   first, second, third and fourth layered sections, each layered section comprising:
      a comfort layer;
      an absorbent layer; and
      an adhesive layer;
   wherein the first channel separates the first and second layered sections from the third and fourth layered sections and the second channel separates the first and fourth layered sections from the second and third layered sections, the channels being flexible and having a thickness less than the thickness of the layered sections;
   wherein the first channel is wider than the second channel.

2. The garment protector of claim 1, wherein the width of at least one of the channels allows the channel to span a cross-stitching of a seam in the piece of clothing so as not to add to the bulk at the seam that a layered section would if over the seam.

3. The garment protector of claim 1, wherein the comfort layer comprises a woven padding layer.

4. The garment protector of claim 1, wherein the absorbent layer comprises an absorbent cotton pad.

5. The garment protector of claim 4, wherein the garment protector is treated with a deodorant, antiperspirant or fragrance compound.

6. The garment protector of claim 1, further comprising a boundary layer.

7. The garment protector of claim 6, wherein the boundary layer is skin color.

8. The garment protector of claim 1, wherein the first channel is more than twice as wide as the second channel.

9. The garment protector of claim 1, wherein the garment protector can adhere to both an arm section and a body section of the piece of clothing.

10. The garment protector of claim 1, wherein the channels are thin flexible members.

11. A garment protector for preserving a piece of clothing comprising:
    a first channel;
    a second channel; and
    first, second, third and fourth absorbent sections;
    wherein the first channel separates the first and second absorbent sections from the third and fourth absorbent sections and the second channel separates the first and fourth absorbent sections from the second and third absorbent sections, the channels being flexible and having a thickness less than the thickness of the absorbent sections and a width that allows at least one of the channels to span a cross-stitching of a seam in the piece of clothing so as not to add to the bulk at the seam that one of the absorbent sections would if over the seam;
    wherein the first and second channels are a single layer.

12. A garment protector for preserving a piece of clothing comprising:
    a first channel;
    a second channel; and
    first, second, third and fourth absorbent sections;
    wherein the first channel separates the first and second absorbent sections from the third and fourth absorbent sections and the second channel separates the first and fourth absorbent sections from the second and third absorbent sections, the channels being flexible and having a thickness less than the thickness of the absorbent sections and a width that allows at least one of the channels to span a cross-stitching of a seam in the piece of clothing so as not to add to the bulk at the seam that one of the absorbent sections would if over the seam;
    wherein the first channel is wider than the second channel.

13. The garment protector of claim 12, wherein the first channel is more than twice as wide as the second channel.

14. The garment protector of claim 12, wherein the first channel is configured for use at a seam between an arm and a body of the piece of clothing.

15. The garment protector of claim 14, wherein the second channel is configured for use at a seam along the arm and along the body of the piece of clothing and wherein the first channel allows for greater flexibility than the second channel.

16. A garment protector for preserving a garment comprising:
    a first channel;
    a second channel; and
    a pad for absorbing moisture in an underarm area of the garment;
    wherein the first channel is configured to attach to the garment along a first seam between an arm and a body of the garment, the first channel spanning the first seam such that the pad is on either side of the first seam but not on the first seam; and
    wherein the second channel is configured to attach to the garment at a second seam, the second seam being along the arm of the garment and at a third seam, the third seam being along the body of the garment, the second channel spanning the second and third seams such that the pad is on either side of the second and third seams but not on the second or third seams;
    wherein the first channel is wider than the second channel and the first and second channels are thinner than the pad.

17. The garment protector of claim 16, wherein the first and second channels are flexible and expandable.

18. The garment protector of claim 16, wherein the first and second channels are a single layer.

19. A garment protector for preserving a piece of clothing comprising:
    a first channel;
    a second channel;
    first, second, third and fourth layered sections, each layered section comprising:
       a comfort layer;
       an absorbent layer; and
       an adhesive layer;
    wherein the first channel separates the first and second layered sections from the third and fourth layered sections and the second channel separates the first and fourth layered sections from the second and third layered sections, the channels being flexible and having a thickness less than the thickness of the layered sections;
    further comprising a boundary layer, wherein the boundary layer comprises a thin flexible plastic layer and the adhesive layer comprises a first adhesive backing on the boundary layer and a second adhesive backing on the first and second channels, wherein the second adhesive backing is more adhesive than the first.

20. A garment protector for preserving a piece of clothing comprising:
- a first channel;
- a second channel; and
- first, second, third and fourth layered sections, each layered section comprising:
  - a comfort layer;
  - an absorbent layer; and
  - an adhesive layer;

wherein the first channel separates the first and second layered sections from the third and fourth layered sections and the second channel separates the first and fourth layered sections from the second and third layered sections, the channels being flexible and having a thickness less than the thickness of the layered sections;

wherein the first and second channels are a single layer.

* * * * *